United States Patent [19]

Starks et al.

[11] 4,120,881

[45] Oct. 17, 1978

[54] PREDOMINANTLY ALIPHATIC LOWER HYDROCARBON MATERIALS FROM CARBONACEOUS SOLIDS

[75] Inventors: Charles M. Starks; Robert G. Jackson; David V. Porchey; Dennis J. Royer, all of Ponca City, Okla.

[73] Assignee: Continental Oil Company, Ponca City, Okla.

[21] Appl. No.: 539,679

[22] Filed: Jan. 9, 1975

[51] Int. Cl.$^2$ ............................................. C07C 27/06
[52] U.S. Cl. .............................. 260/449.6 R; 252/373; 48/202; 260/449.6 M
[58] Field of Search ..................... 260/449.6; 252/373; 48/202

[56] References Cited

U.S. PATENT DOCUMENTS 3,779,725   12/1973   Hegarty et al. ..................... 252/373

Primary Examiner—A. Siegel

Attorney, Agent, or Firm—Cortlan R. Schupbach, Jr.

[57] ABSTRACT

Predominantly aliphatic lower hydrocarbon materials may be obtained from carbonaceous solids by a sequence of steps comprising gasifying the carbonaceous solids, combining the gasification product stream with first and second internal recycle streams, separating certain impurities from the combined stream followed by cooling to liquefy and separate the hydrocarbon materials, directly reacting the remaining carbon monoxide and hydrogen in the presence of a catalyst to produce a first internal recycle stream, fractionating the separated hydrocarbon materials to separate and recover the predominantly aliphatic lower hydrocarbon materials from the higher hydrocarbon materials, subjecting the higher hydrocarbon materials to steam cracking to produce a second internal recycle stream, and recycling the internal recycle streams for combination with the gasification product stream as noted above.

7 Claims, No Drawings

PREDOMINANTLY ALIPHATIC LOWER HYDROCARBON MATERIALS FROM CARBONACEOUS SOLIDS

This invention relates to an integrated process for producing predominantly aliphatic lower hydrocarbon materials from carbonaceous solids.

In the past, hydrocarbons of a predominantly aliphatic nature, both paraffinic and olefinic, have generally been obtained from distillation and separation of crude petroleum and natural gas and from cracking petroleum fractions. Quite apparently, with the decline of available reserves of crude petroleum and natural gas, there is a need for alternative means for producing such predominantly aliphatic hydrocarbons which are not dependent upon natural gas and petroleum feedstocks.

Another source of hydrocarbons has been from distillation of carbonaceous solids, such as coal. However, these hydrocarbons are highly aromatic and constitute only a minor percentage of the initial charge of solids.

The Synthol process is also known (Chem. Engr. Prog., 1960, Vol. 56, No. 4, pp 39-48) for producing hydrocarbons from coal, some of which are aliphatic. In this process, coal is initially gasified, then purified and used as a feedstock to both an Arge synthesis and a Kellogg synthesis. The purified effluent may be used directly as a feedstock to an Arge synthesis for producing primarily diesel oil and waxes. However, in the Kellogg synthesis wherein gasoline is primarily produced, the purified effluent is first passed through a reforming section. Consequently, while the process may be operated to produce some aliphatic hydrocarbons, it is necessarily relatively complicated.

In accordance with this invention, there is provided an integrated process wherein lower hydrocarbons and some oxygenated lower hydrocarbons of a predominantly aliphatic nature are produced from carbonaceous solids by a combination of gasification and Fischer-Tropsch synthesis without reformation. Briefly described, the integrated process involves gasification of a carbonaceous solid under suitable conditions to produce a gasification product stream of which the major portion is formed by carbon monoxide, carbon dioxide, hydrogen, and water, with a minor portion being hydrocarbons of a predominantly aliphatic nature. Since most carbonaceous solids contain sulfur materials, some sulfur compounds, such as hydrogen sulfide and carbonyl sulfide, will also be present. The gasification product stream is then combined with two internal recycle streams rich in hydrocarbon materials of a predominantly aliphatic nature, and the combined stream is subjected to conventional separation treatments for removal of most sulfur compounds, carbon dioxide, and water. The partially purified stream is then subjected to cryogenic separation to separate the predominantly aliphatic hydrocarbon materials from the carbon monoxide and hydrogen. The latter are then used as a feedstock to a Fischer-Tropsch synthesis and are converted to a product stream rich in hydrocarbon materials of a predominantly aliphatic nature which becomes one of the internal recycle streams referred to above. These hydrocarbon materials, paraffinic and olefinic, include both hydrocarbons and some oxygenated hydrocarbons. The predominantly aliphatic hydrocarbon materials separated cryogenically are fractionated to separate the lower hydrocarbon materials from the higher hydrocarbon materials. Obviously, this separation may involve several fractions as desired. The lower hydrocarbon materials are recovered as the predominantly aliphatic product, while the higher hydrocarbon materials are subjected to steam cracking to produce the other internal recycle stream.

The invention is applicable to carbonaceous solids in general, such as coke, oil shale, tar sands, char, lignite, anthracite, and bituminous coals. According to the invention, these carbonaceous solids are gasified by reaction with steam as is known in the art. In general, gasification is accomplished by feeding the carbonaceous solids, preferably in a particulate form, together with steam to a gasification zone operating at temperatures in the range of 500° C to 2,100° C, preferably 550° C to 1,300° C, and pressures of about 1 atmosphere to 300 atmospheres, preferably 1 atmosphere to 100 atmospheres. The ratio of steam (water) to carbonaceous solids is generally in the range of about 0.1 to 3 pounds of steam per pound of carbonaceous solids, preferably 0.5 to 2 pounds of steam on the same basis. Higher quantities of water will tend to excessively increase the amount of carbon dioxide in the product stream at the expense of carbon monoxide, the carbon monoxide being desirable for the subsequent Fischer-Tropsch synthesis. Lower quantities of water tend to result in insufficient conversion of the carbonaceous solids for an efficient process.

The temperatures in the gasification zone may be obtained by any suitable external heating means, such as gas heaters or electrical resistance means. Alternatively, and as is usually the case, the temperatures may be generated in situ by introducing an oxygen-containing gas along with the carbonaceous solids and steam to the gasification zone. This will result in some combustion taking place in the zone and generating the necessary thermal energy to sustain the desired temperatures. It is pointed out that the combustion region in the gasification zone may operate at temperatures somewhat above those mentioned heretofore. Some water will also be produced by the combustion and can be taken into consideration in adjusting the quantity of outside steam fed to the zone.

The oxygen-containing gas can be provided by any suitable source and can contain some inert materials. Quite obviously, the inerts should be maintained as low as possible so as to avoid the necessity of handling large volumes of materials which do not contribute to the efficiency of the process. Preferably, an oxygen-rich stream containing at least 95 mol percent oxygen is used, such as that provided by a Linde-Frankl process. The amount of oxygen supplied to the gasification zone may generally range from about 0.1 to 1 pound of oxygen per pound of carbonaceous solids, preferably in the range of 0.2 to 0.8 pound of oxygen on the same basis.

The initial effluent from the gasifier may contain tars and related heavy materials such as result from volatilization of coal. Typical of these materials are highly aromatic compounds, phenolics, etc. Usually, when tars and the like are present, a quenching stage, such as with water, is employed to condense them from the effluent, and they are then recycled back to the gasifier. Not all gasifications of carbonaceous materials result in tars being present in the initial effluent, and thus quenching is not always necessary. Quenching may also serve to remove particulate solids carry-over or, alternatively, a conventional solids separator may be used if it is desired or necessary to remove such solids for recycle or other disposal. All of this is well known in the art.

In any event, a gasification product stream is obtained from the gasification step in the overall process. The gasification product stream is predominantly carbon monoxide, carbon dioxide, hydrogen, and water, although some hydrocarbons of a predominantly aliphatic nature are present along with some tars. With sulfur-containing carbonaceous solids, some sulfur compounds, such as hydrogen sulfide and carbonyl sulfide, will be formed.

The gasification product stream is combined with the internal recycle streams which are rich in hydrocarbon materials of a predominantly aliphatic nature. These recycle streams are obtained as the effluent from a Fischer-Tropsch synthesis and as the effluent from a conventional steam cracking step further downstream and to be described in further detail hereinafter. As noted above, the predominantly aliphatic hydrocarbon materials, paraffinic and olefinic, include both hydrocarbons and some oxygenated hydrocarbons. In addition to the hydrocarbon materials, the recycle stream also contains carbon monoxide, carbon dioxide, water, and hydrogen.

The combined streams, hereinafter referred to as the crude product stream, are then subjected to separation to remove carbon dioxide, sulfur compounds, and water. This may be accomplished according to known techniques. For example, water may be removed by simply cooling the crude product steam to condense the major portion of the water followed by passing the crude product stream through a dryer containing a desiccant, such as alumina or silica gel. Carbon dioxide and some sulfur compounds may be removed by such conventional techniques as adsorption with a suitable agent; e.g., an aqueous solution of an amine, particularly monoethanolamine, or by treating with a hot aqueous solution of potassium carbonate, or by a combination of such processes (see U.S. Pat. No. 3,684,689 for applicable techniques). Alternatively, carbon dioxide and sulfur compounds, such as hydrogen sulfide and carbonyl sulfide, may be removed simultaneously by means of the Rectisol and Purisol systems as described in Industrial and Engineering Chemistry, Volume 62, No. 7, July, 1970, pp 39–43. If desired, sulfur may be recovered from the separation liquids by the well-known Claus process.

The thus purified product stream, containing essentially only hydrocarbon materials, carbon monoxide and hydrogen, is then subjected to cryogenic separation. In such cryogenic separation, the purified product stream is cooled to a temperature below the condensation temperature of methane, the lowest boiling hydrocarbon material present in the product stream, thus effecting condensation of the hydrocarbon materials and separation from the carbon monoxide and hydrogen. Cryogenic systems for performing this separation are known in the art. The separated hydrocarbon materials are then subjected to further separation and treatment as described hereinafter.

The hydrogen and carbon monoxide remaining after separation of the hydrocarbon materials are used as a direct feedstock for the Fischer-Tropsch synthesis step of the process. This synthesis is well known in the art and is generally described hereinbelow.

The feedstock to the Fischer-Tropsch synthesis should have a mol ratio of hydrogen to carbon monoxide of at least 1/1, and preferably at least 1.5/1. In most instances, the hydrogen and carbon monoxide from the cryogenic separator will be at a mol ratio much higher than this, but if at any time the ratio falls below the 1/1 level, additional hydrogen from a suitable outside source should be added to bring the ratio to the proper minimum level.

Low amounts of hydrogen decrease the reaction rate and, perhaps more importantly, tend to result in some disassociation of the carbon monoxide to carbon dioxide and elemental carbon. The formation of carbon is undesirable as it deposits out on the reactor walls and catalyst. This results in decreased heat transfer, a factor which may be significant in view of the exothermic nature of the reaction, and a decreased activity of the catalyst. As the mol ratio of hydrogen to carbon monoxide increases, the rate of reaction generally increases up to a point after which it either remains somewhat constant or even tapers off. In addition, high amounts of hydrogen also generally tend to result in lower average molecular weight hydrocarbon materials being formed with paraffinic compounds favored over olefinic compounds. Another factor to be considered with high amounts of hydrogen is that the unconsumed hydrogen must be carried through the recycle steps of the process since the effluent of the Fischer-Tropsch synthesis is recycled. Considering all of these aspects, it is generally desired to operate the process with a mol ratio of hydrogen to carbon monoxide of not greater than about 5/1, and preferably in the range of about 2/1 to 4/1. Obviously, a suitable outside source may be employed to introduce additional carbon monoxide or hydrogen to provide the desired mol ratio.

It is pointed out that the hydrogen-carbon monoxide feedstock from the cryogenic separator may contain some hydrocarbon materials and may even contain some water without adversely affecting the Fischer-Tropsch synthesis step. Sulfur compounds, such as hydrogen sulfide and carbonyl sulfide, are undesirable as they tend to deactivate the synthesis catalyst. These, however, are removed or reduced to a sufficiently low level with the earlier purification steps.

The Fischer-Tropsch synthesis may be conducted at temperatures in the range of about 150° C to about 450° C. Lower temperatures tend to result in higher molecular weight products which may cause fouling of the catalyst or reaction zone. On the other hand, higher temperatures may tend to result in carbonization which likewise may cause catalyst fouling. Preferred temperatures are in the range of 200° C to 400° C, with the most preferred temperatures ranging from 250° C to 350° C.

Pressures as low as atmospheric pressure may be employed, but the reaction rate is relatively slow at low pressures. Higher pressures may also be used with the primary considerations being equipment design, possible reactor and catalyst fouling due to the fact that higher pressures tend to result in higher molecular weight products, and reaction control since increased pressure increases the reaction rate. Generally, pressures in the range of 5 to 75 atmospheres gauge will be used, preferably 10 to 30 atmospheres gauge.

The reaction may be conducted in a zone containing a conventional fixed or fluidized (fixed or entrained types) catalyst bed. Normally, the fluidized bed is employed. Space velocities in the range of about 500 to 50,000 volumes of feedstock/volume of catalyst/hour at standard temperature and pressure conditions may be used, preferably in the range of 5,000 to 10,000 V/V/hr STP.

The catalysts useful for the reaction include any Fischer-Tropsch catalyst containing iron, cobalt, nickel, or ruthenium. These catalysts are well known in the art, being described in the Fischer-Tropsch and Related Syntheses by Storch et al, John Wiley and Sons, 1951, Chapter 3, all of which is incorporated herein by reference. As also well known in the art and described in the referenced text, these catalysts may be supported and may be promoted or activated by numerous materials. All of this is intended to be encompassed by the phrase "Fischer-Tropsch catalyst" as used herein. Further examples of suitable Fischer-Tropsch catalysts appear in U.S. Pat. No. 2,543,327 and U.S. Pat. No. 2,944,988, also incorporated herein by reference.

A particularly preferred Fischer-Tropsch catalyst is one containing iron and promoted or activated with alumina, magnesium oxide, calcium oxide, potassium oxide, silica, manganese oxide, thoria, titania, molybdenum oxide, or mixtures thereof. Suitable sources of iron component include mill scale and magnetite with the latter already containing some of the promoters or activators.

The synthesis is preferably carried out under conditions within the ranges described above to a conversion of carbon monoxide in the feedstock of at least 50 percent. The effluent from the Fischer-Tropsch synthesis contains hydrocarbon materials which include both hydrocarbons and some oxygenated hydrocarbons and are predominantly aliphatic. By aliphatic, it is meant paraffinic and olefinic. Very little aromatic content is present. The effluent will, of course, additionally contain carbon monoxide, hydrogen, carbon dioxide, and water. The total effluent is then recycled to the process and combined with the gasification product stream prior to processing through the separation zone.

The predominantly aliphatic hydrocarbon materials which are separated in the cryogenic separation step are fractionally distilled to separate the desired molecular weight products. For example, methane may be initially separated as it is the lowest boiling followed sequentially by ethylene, ethane, propylene, propane, etc, as desired. Product streams of primarily a single component or a mixture of components may be withdrawn. The remaining hydrocarbon materials not desired as products, usually the higher hydrocarbon materials, such as the $C_3$, $C_4$, or $C_5$ and higher materials, are then passed to a conventional steam-cracking stage for cracking to lower aliphatic hydrocarbon materials and subsequent recycle back to the process to be combined with the gasification product stream prior to processing through the cryogenic separation zone.

The cracking step is accomplished with steam and high temperatures as is conventionally known in the art. In general, the cracking may be carried out with about 0.2 to 1.5 pounds of steam per pound of hydrocarbon materials at temperatures ranging from about 750° C to 950° C and partial pressures of the hydrocarbon materials of up to 2 atmospheres. If the hydrocarbon materials being cracked contain only $C_3$ and higher materials, it is preferred that the hydrocarbon partial pressure employed be up to only 1 atmosphere. Residence times in the range of 0.01 to 10 seconds, preferably 0.05 to 1 second, may be satisfactorily employed.

As mentioned hereinbefore, the effluent from the cracking step is then recycled to the process and combined with the gasification product stream along with the Fischer-Tropsch effluent, and the combined stream is subjected to the separation processing described hereinbefore.

The following example will serve to further illustrate the process of the invention:

Example

A small charge of coal is placed in a cylindrical stirred reactor and combustion of this charge is begun with oxygen and suitable temperatures. After starting combustion of the initial charge of coal, coal gasification is conducted by feeding 33.5 pounds of pulverized coal per hour into the top of the reactor while simultaneously feeding oxygen (308 SCF/hour) and steam (55 pounds/hour) into the bottom of the reactor. As the coal, oxygen, and steam supply rates are brought up to these values, the pressure of the reactor is also allowed to gradually increase to an operating pressure of about 350 psig (about 25 atmospheres). After several hours of steady operation, the temperature profile of the reactor becomes approximately steady (decreasing from about 1,700° to 2,100° C at the bottom of the reactor to about 500° to 600° C at the top of the reactor) and the gasification product stream (after quenching and removing tars) consists of a gas stream approximately 2,000 SCF per hour and having the composition of 35.9 percent steam, 17.8 percent $CO_2$, 15.3 percent CO, 24.2 percent $H_2$, 6.4 percent $CH_4$, 0.2 percent $H_2S$, 0.3 percent $C_2H_6$, and 0.2 percent $C_2H_4$ (all by volume).

According to the invention, it is contemplated that this gasification product stream is mixed with the product gas from the Fischer-Tropsch reactor (see below) and with the products of the cracking furnaces (see below). The combined stream is cooled to about 25° to 75° C under about 325 psig pressure to condense and separate water. The gas stream is conducted into a countercurrent absorption column containing ethanolamine and water wherein $CO_2$ and $H_2S$ are selectively removed. The clean gas, under approximately 325 psig pressure, is cooled through a series of heat exchangers in the cryogenic separator to temperatures in the range of $-100°$ C to $-160°$ C where most of the methane and higher hydrocarbons present condense to liquids and are separated from hydrogen, carbon monoxide, and a small fraction of methane which is not condensed but remains gaseous. The liquefied hydrocarbons are then fractionally distilled to a methane cut, an ethylene cut (contains a small amount of acetylene), an ethane cut, and a propylene cut, while propane and higher boiling materials are left for introduction to the cracking furnaces.

The invention contemplates conducting the gaseous product from the cryogenic separator to the Fischer-Tropsch reactor where hydrogen and carbon monoxide are converted to hydrocarbons. A simulated gaseous product formed of H and CO in a molar ratio of about 3/1 is conducted into the reactor containing a fluidized catalyst prepared by hydrogenating and carbiding a pulverized fused mixture of magnetite, potassium carbonate, and alumina. The Fischer-Tropsch reaction is maintained at a temperature of about 388° C, pressures of about 300 psig, and with a space velocity of about 8,000 V/V/hour STP. The product from this reaction, after passing through a cyclone to remove entrained catalyst, is compressed to about 350 psig and recycled back to mix with the gas from the gasifier and the product of the cracking furnaces according to the invention and as noted above. The product from the Fischer-Tropsch reaction has the following approximate composition: 21.7 percent $H_2$, 0.8 percent CO, 27.1 percent $CH_4$, 8.6 percent ethylene and ethane, 7.3 percent propylene and propane, 4.0 percent $C_4$ hydrocarbon materials, 2.4 percent $C_5$ hydrocarbon materials, 5.0 percent $C_{6+}$ hydrocarbon materials, 4.8 percent $CO_2$, and 18.3 percent $H_2O$.

The ethane cut and the propane and higher boiling hydrocarbons from the cryogenic separator are introduced to cracking furnaces operated under two sets of conditions to optimize the yield of products. In the ethane cracking furnace, the ethane cut along with 0.2 moles of water per mole of ethane and 50 ppm $H_2S$ is cracked in a tubular furnace at about 890° C coil outlet temperature, 22 psia coil outlet pressure, and an average contact time of about 0.5 second. The product from this cracking reaction contains about 20 mole percent water (steam), 26 percent $H_2$, 4 percent methane, 0.2 percent acetylene, 26 percent ethylene, 23 percent ethane, 0.4 percent propylene, and 0.8 percent higher boiling products. The propane and higher boiling hydrocarbons from the cryogenic separation are cracked in the other cracking furnace, along with about 0.6 mole of water per mole of hydrocarbon feed and 50 ppm $H_2S$, at about 775 to 800° C coil outlet temperature, 10 psia outlet partial pressure of hydrocarbons, and a contact time of about 1.3 seconds. The product from this cracking furnace contains about 38 mole percent water, 8 percent hydrogen, 21 percent methane, 0.3 percent acetylene, 15.3 percent ethylene, 4 percent ethane, 7 percent propylene, and 6.4 percent higher boiling components. The product streams from both the ethane cracking furnace and the propane and higher boiling hydrocabon cracking furnace are quenched with water to a temperature of less than 500° C and are then combined with the gasification product stream and the Fischer-Tropsch reactor effluent as described hereinbefore.

Thus, the products from the overall process depicted by this example are the methane cut, the ethylene cut, and the propylene cut from the cryogenic separator.

Thus, having described the invention in detail, it will be understood by those skilled in the art that certain variations and modifications may be made within the spirit and scope of the invention as described herein and defined in the appended claims.

We claim:
1. A process comprising:
   (a) gasifying carbonaceous solids with from about 0.1 to about 3 pounds of steam per pound of said solids at temperatures in the range of 500° C to 2,100° C and pressures of atmospheric to 1,000 atmospheres to form a gasification product stream containing a mixture of water, carbon dioxide, carbon monoxide, hydrogen, sulfur compounds and hydrocarbon materials of a predominantly aliphatic type,
   (b) combining the gasification product stream with first and second internal recycle streams rich in hydrocarbon materials of a predominantly aliphatic type to form a crude product stream,
   (c) removing water, carbon dioxide and sulfur compounds from the crude product stream to form a purified product stream containing essentially only hydrocarbon materials, carbon monoxide and hydrogen,
   (d) cooling the purified product stream to liquefy and separate the hydrocarbon materials from the carbon monoxide and hydrogen,
   (e) directly introducing the carbon monoxide and hydrogen from step (d) to a catalytic reaction zone and reacting the carbon monoxide and hydrogen in said zone to produce a first internal recycle stream rich in hydrocarbon materials of a predominantly aliphatic type, said reaction being conducted under conditions of temperatures in the range of about 150° C to 450° C, pressures in the range of atmospheric to 75 atmospheres and space velocities in the range of 500 to 50,000 V/V/hr STP, in the presence of a Fischer-Tropsch catalyst containing iron, cobalt, nickel or ruthenium,
   (f) recycling the first internal recycle stream of step (e) back to step (b) of the process,
   (g) fractionally separating the hydrocarbon materials of step (d) into product hydrocarbon materials and residual higher hydrocarbon materials,
   (h) directly introducing the residual hydrocarbon materials to a cracking zone and cracking said hydrocarbon materials to produce a second internal recycle stream, said cracking being carried out using about 0.2 to 1.5 pounds of steam per pound of hydrocarbon materials, temperatures of 750° C to 950° C, hydrocarbon materials partial pressures up to about 2 atmospheres and residence times of 0.01 to 10 seconds, and
   (i) recycling the second internal recycle stream of step (h) back to step (b) of the process.

2. A process according to claim 1 wherein the carbonaceous solids are coke, oil shale, tar sands, char, lignite, or coal.

3. A process according to claim 2 wherein 0.1 to 1 pound of oxygen per pound of carbonaceous solids is additionally employed in the gasification of step (a).

4. A process according to claim 3 when temperatures in the range of 550° C to 1,300° C, pressures in the range of atmospheric to 100 atmospheres and 0.5 to 2 pounds of steam per pound of carbonaceous solids are employed in the gasification of step (a).

5. A process according to claim 4 wherein 0.2 to 0.8 pound of oxygen per pound of carbonaceous solids is additionally employed in the gasification of step (a).

6. A process according to claim 3 wherein the reaction of step (e) is conducted at temperatures of 200° C to 400° C, pressures of 5 to 75 atmospheres gauge and space velocities of 5,000 to 10,000 V/V/hr STP.

7. A process according to claim 6 wherein the cracking of step (h) is carried out a hydrocarbon materials partial pressures of up to 1 atmosphere and residence times of 0.05 to 1 second.

* * * * *